(12) United States Patent
Corte et al.

(10) Patent No.: US 7,456,188 B1
(45) Date of Patent: Nov. 25, 2008

(54) C-5 SUBSTITUTED QUINAZOLINONE DERIVATIVES AS SELECTIVE ESTROGEN RECEPTOR BETA MODULATORS

(75) Inventors: James R. Corte, Lawrenceville, NJ (US); John K. Dickson, Apex, NC (US); Timur Gungor, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 39 days.

(21) Appl. No.: 11/411,456

(22) Filed: Apr. 26, 2006

Related U.S. Application Data

(60) Provisional application No. 60/675,693, filed on Apr. 28, 2005.

(51) Int. Cl.
*A61K 31/517* (2006.01)
*C07D 239/88* (2006.01)

(52) U.S. Cl. .................. 514/266.21; 514/266.31; 544/284; 544/287

(58) Field of Classification Search ............ 514/266.21, 514/266.31; 544/284, 287
See application file for complete search history.

(56) References Cited

U.S. PATENT DOCUMENTS

| 4,411,890 A | 10/1983 | Momany |
| 2003/0220227 A1 | 11/2003 | Gungor et al. |

FOREIGN PATENT DOCUMENTS

| JP | 10-259176 A | * | 9/1998 |
| WO | WO 89/07110 | | 8/1989 |
| WO | WO 89/07111 | | 8/1989 |
| WO | WO 93/04081 | | 3/1993 |
| WO | WO00/07996 | | 2/2000 |

OTHER PUBLICATIONS

Vippagunta, S.R. et al., "Crystalline solids", Adv. Drug Del. Reviews, (2001), vol. 48, pp. 3-26.*
Chemical Abstract, 1998, vol. 129, Abstract # 310895 (English Abstract for JP 10-259176).*
Güngör, T. et al., "Synthesis and Characterization of 3-Arylquinazolinone and 3-Arylluinazolinethione Derivatives as Selective Estrogen Receptor Beta Modulators", J. Med. Chem., vol. 49, pp. 2440-2455 (2006).
Sun, J. et al., "Novel Ligands that Function as Selective Estrogens or Antiestrogens for Estrogen Receptor-α or Estrogen Receptor-β*", Endocrinology, vol. 140(2), pp. 800-804 (1999).
Zhou, H. et al., "Synthesis and Evaluation of Estrogen Receptor Ligands with Bridged Oxabicyclic Cores Containing a Diarylethylene Motif: Estrogen Antagonists of Unusual Structure", J. Med. Chem., vol. 48, pp. 7261-7274 (2005).
Edwards, J.P. et al., "Nonsteroidal androgen receptor agonists based on 4-(Trifluoromethyl)-2H-Pyrano[3,2-g] Quinolin-2-One", Bioorganic & Medicinal Chemistry Letters, vol. 9, pp. 1003-1008 (1999).
Hamann, L.G. et al., Discovery of a Potent, Orally Active, Nonsteroidal Androgen Receptor Agonist: 4-Ethyl-1,2,3,4-tetrahydro-6-(trifluoromethyl)-8-pyridono[5,6-g]-quinoline (LG121071), J. Med. Chem, (1999), vol. 42, pp. 210-212.
Kuiper, G. et al., "Interaction of Estrogenic Chemicals and Phytoestrogens with Estrogen Receptor β". Endocrinology, vol. 139(10), pp. 4252-4263 (1998).
Newman, H. et al., "The Synthesis of the Ring-B Sulfur Analog of Epigriseofulvin", The J. of Organic Chemistry, vol. 34(11), pp. 3484-3491 (1969).

* cited by examiner

*Primary Examiner*—James O. Wilson
*Assistant Examiner*—Tamthom N Truong
(74) *Attorney, Agent, or Firm*—Burton Rodney; Maureen S. Gibbons

(57) ABSTRACT

The present application describes compounds according to Formula I, wherein Q, $R^1$, $R^2$ and X are described herein, that are useful as Estrogen Receptor Beta (ERβ) modulators. Additionally, the present application describes pharmaceutical compositions containing the compounds according to Formula I and optionally additional therapeutic agents. Finally, the present application describes methods utilizing the compounds according to Formula I for modulating the function of ERβ in the treatment of diseases and disorders associated with ERβ such as, for example, bone disorders; cardiovascular diseases; hypercholesterolemia; hypertriglyceridemia; vasomotor disorders; urogenital disorders; prostatic hypertrophy; endometrial hyperplasia; cancer and central nervous system disorders, such as, neurodegenerative disorders.

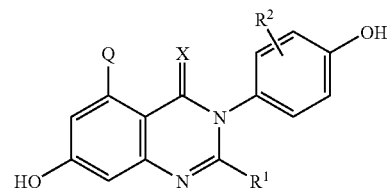

13 Claims, No Drawings

C-5 SUBSTITUTED QUINAZOLINONE DERIVATIVES AS SELECTIVE ESTROGEN RECEPTOR BETA MODULATORS

RELATED APPLICATION

This application claims priority benefit under Title 35 § 119(e) of U.S. Provisional Application No. 60/675,693, filed Apr. 28, 2005, the contents of which are herein incorporated by reference.

BACKGROUND OF THE INVENTION

The estrogen hormone has a broad spectrum of effects on tissues in both females and males. Many of these biological effects are positive, including maintenance of bone density, cardiovascular protection, central nervous system (CNS) function and the protection of organ systems from the effects of aging. However, in addition to its positive effects, estrogen also is a potent growth factor in the breast and endometrium that increases the risk of cancer.

Until recently, it was assumed that estrogen binds to a single estrogen receptor (ER) in cells. However, a second estrogen receptor, ER beta (ERβ), has been identified and cloned, with the original ER being renamed ER alpha (ERα). *Endocrinology* 1998 139 4252-4263. ERβ and ERα share about a 50% identity in the ligand-binding domain and only 20% homology in their amino-terminal transactivation domain. The difference in the identity of the two ER subtypes accounts for the fact that small compounds may demonstrate a higher affinity to bind to one subtype over the other.

Further, ERβ and ERα are believed to have varied distributions and functions in different tissues. For example, in rats, ERβ is strongly expressed in brain, bone and vascular epithelium, but weakly expressed in uterus and breast, relative to ERα. Further, ERα knockout mice are sterile and exhibit little or no evidence of hormone responsiveness of reproductive tissues. In contrast, ERβ knockout mice are fertile and exhibit normal development and function of breast and uterine tissue. These observations suggest that selectively targeting ERβ over ERα could confer beneficial effects in several important diseases, such as Alzheimer's disease, anxiety disorders, depressive disorders, osteoporosis and cardiovascular diseases, without the liability of reproductive system side effects. Selective effects on ERβ expressing tissues over uterus and breast could be achieved by agents that selectively interact with ERβ over ERα.

Accordingly, it would be advantageous to develop a series of novel compounds, which selectively modulate ERβ receptors and may be employed to treat a variety of estrogen-dependent pathological conditions.

DETAILED DESCRIPTION OF THE INVENTION

The present application describes compounds according to Formula I, wherein Q, $R^1$, $R^2$ and X are described herein, that are useful as Estrogen Receptor Beta (ERβ) modulators. Additionally, the present application describes pharmaceutical compositions containing the compounds according to Formula I and optionally additional therapeutic agents. Finally, the present application describes methods utilizing the compounds according to Formula I for modulating the function of ERβ in the treatment of diseases and disorders associated with ERβ such as, for example, bone disorders; cardiovascular diseases; hypercholesterolemia; hypertriglyceridemia; vasomotor disorders; urogenital disorders; prostatic hypertrophy; endometrial hyperplasia; cancer and central nervous system disorders, such as, neurodegenerative disorders.

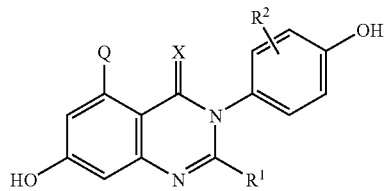

DEFINITIONS

The following definitions apply to the terms as used throughout this specification, unless otherwise limited in specific instances.

The term "alkyl" or "alk" as employed herein, alone or as part of another group, includes both straight and branched chain hydrocarbons, containing 1 to 20 carbons, preferably 1 to 10 carbons, more preferably 1 to 8 in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. "Substituted alkyl" includes an alkyl group optionally substituted with one or more functional groups which are attached commonly to such chains, such as, but not limited to, halo, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, optionally substituted amino, hydroxy, hydroxyalkyl, acyl, oxo, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl, alkylthio and the like.

The term "cycloalkyl" means a cycloalkyl group preferably containing 3 to 8 carbon atoms, such as cyclopropyl, cyclobutyl, cyclopentyl, cyclohexyl. Any of such groups may be optionally substituted with one or more substituents, such as, but not limited to any of the substituents described above for substituted alkyl.

As used herein, the term "benzyl" refers to $CH_2C_6H_5$.

The term "allyl" as used herein, refers to a $-CH_2CH=CH_2$.

As used herein, the term "halo" or "halogen" refers to fluorine, chlorine, bromine and iodine.

The term "modulator" refers to a chemical compound with capacity to either enhance (e.g., "agonist" activity) or inhibit (e.g., "antagonist" activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:

a) *The Practice of Medicinal Chemistry*, Camille G. Wermuth et al., Ch. 31, (Academic Press, 1996);

b) *Design of Prodrugs*, edited by H. Bundgaard, (Elsevier, 1985); and c) *A Textbook of Drug Design and Development*, P. Krogsgaard-Larson and H. Bundgaard, eds. Ch. 5, pp. 113-191 (Harwood Academic Publishers, 1991). Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center.

Preferred salts of the compounds of formula I which contain a basic group include monohydrochloride, hydrogensulfate, methanesulfonate, phosphate or nitrate.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods, for example, chromatographic or fractional crystallization.

The compounds of the invention may be prepared as shown in the following reaction schemes and description thereof, as well as relevant published literature procedures available to those skilled in the art. Exemplary reagents and procedures for these reactions appear hereinafter and in the working Examples.

Compounds of the formula I where X=O (Ia) may be prepared by substitution of the triflate in compound II with an appropriate organometallic reagent under palladium-mediated catalysis (R=H), or by substitution on a protected (R=Me) analog of II followed by demethylation. Appropriate organometallic reagents may include compounds where the Q group is bonded to a organometallic functional group such as $B(OH)_2$, B, $SnBu_3$, Zn, $ZnX_2$, or MgX (X=Cl, Br, or I). Reagents which catalyze the substitution reaction are typically palladium-based, such as $(Ph_3P)_4Pd$, $Pd(dppf)Cl_2$, $Pd_2(dba)_3$, $POPd_2$, $PXPd_2$, or $Pd(OAc)_2$, but may also contain other metals (e.g. Ni). Demethylation may be accomplished by treatment with, for example, $BBr_3$, 48% HBr, NaSEt, LiCl, or pyridinium hydrochloride.

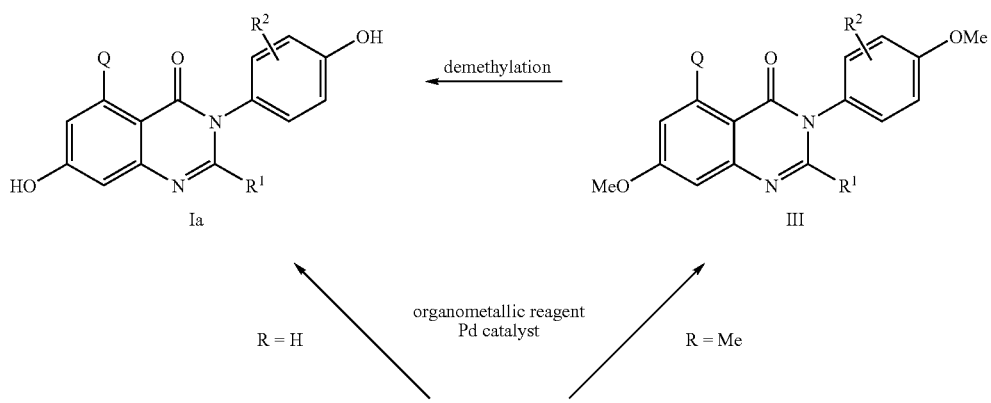

SCHEME 1

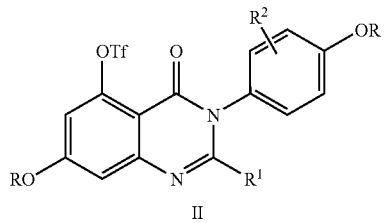

II

Compounds of the formula III which contain an amide at Q (IIIb) may be prepared from esters IIIa by hydrolysis of the ester with a base such as NaOH or an acid such as HCl to provide the carboxylic acid, which is coupled to an appropriate $R^4R^5NH$ amine through the reaction of standard acylation reagents, such as 1-(3-dimethylaminopropyl)-3-ethylcarbodiimide (EDC) and 1-hydroxybenztriazole (HOBt), or bromotripyrrolidinophosphonium hexafluorophosphate (PyBroP). Formation of compounds of the formula IIIc or IIId may be accomplished by reduction of the corresponding ester (IIIa) or amide (IIIb) with a hydride reagent such as $LiAlH_4$, DIBAL, or the like. Under non-selective reducing conditions where the quinazolinone N—C=N bond is also reduced, selective reoxidation to the quinazolinone may be accomplished with a strong oxidizing agent such as DDQ to provide IIIc or IIId. The amine IIId may also be prepared by transformation of the OH group of compounds of the formula IIIc into an $NH_2$ group via a variety of methods known in the literature. Alternatively, compounds IIId may arise from reduction of a nitrile (Q=CN) with a hydride reagent such as $LiAlH_4$, or under hydrogenation conditions (e.g. hydrogen, palladium on carbon).

SCHEME 2

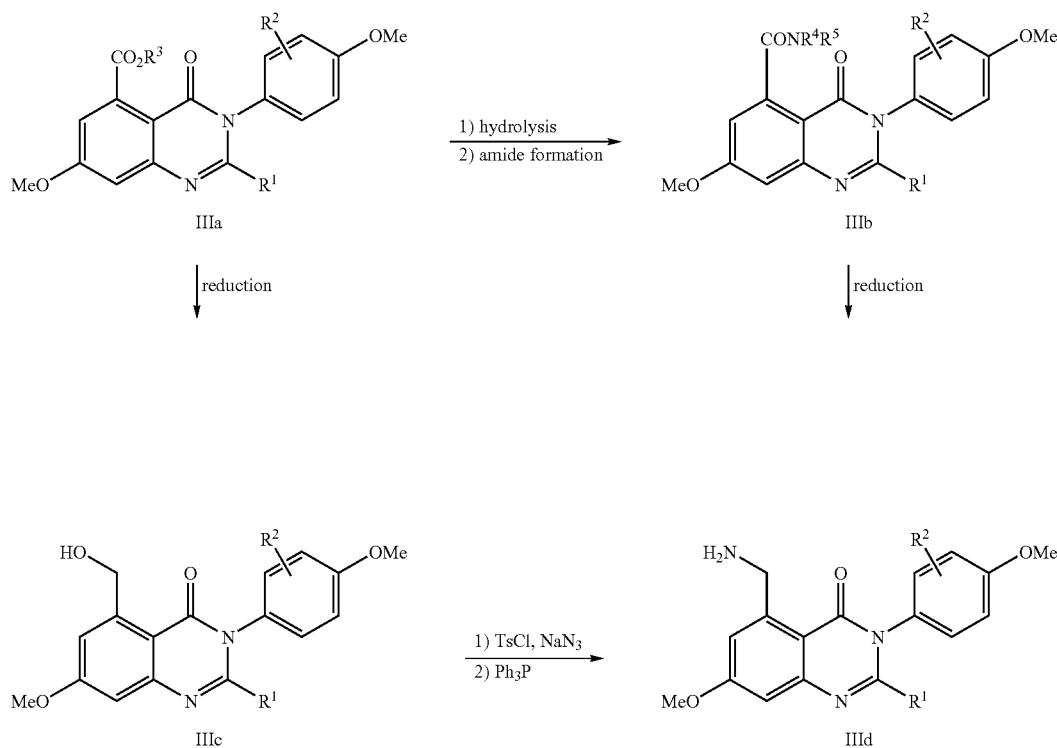

Compounds of the formula I where X=S (Ib) may be prepared by demethylation of compounds of the formula IV by methods described herein. Compounds IV may be prepared by thiation of the appropriate quinazolinone III.

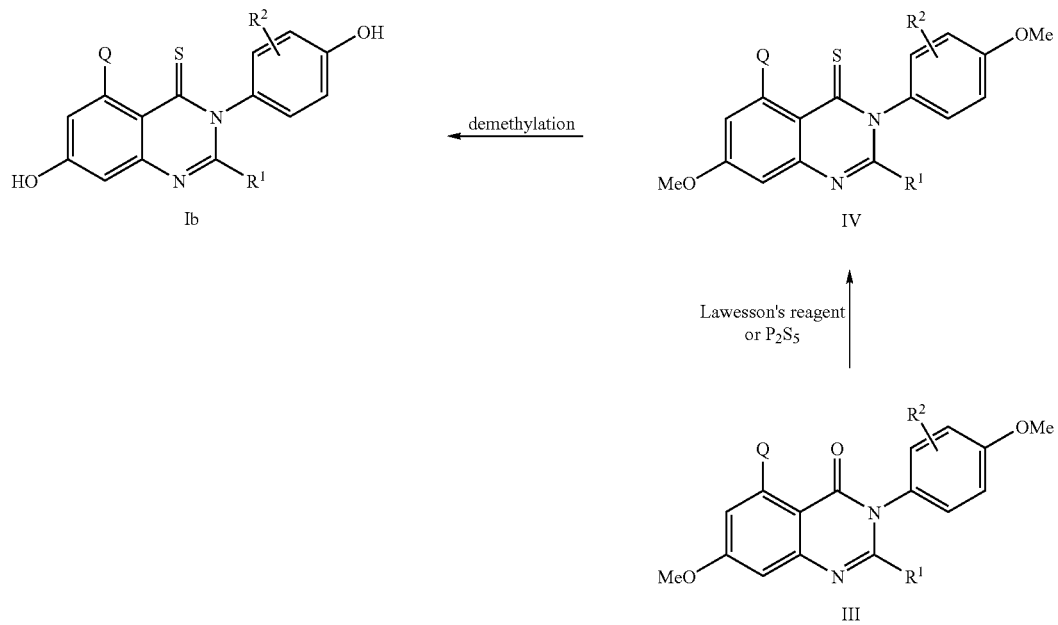

SCHEME 3

Compounds of the formula II where R=H (IIa) may be prepared by demethylation of compounds of the formula IIb by methods described herein. Compounds of the formula IIb may arise from selective mono-demethylation of compounds of the formula V, followed by treatment with a triflating agent such as triflic anhydride or N-phenyltrifluoromethanesulfonimide in the presence of a base. Selective demethylation may be accomplished by treatment with one equivalent of a demethylating agent such as $BBr_3$, or by reaction with LiX (X=Cl or Br) in a polar solvent such as DMF or DMSO.

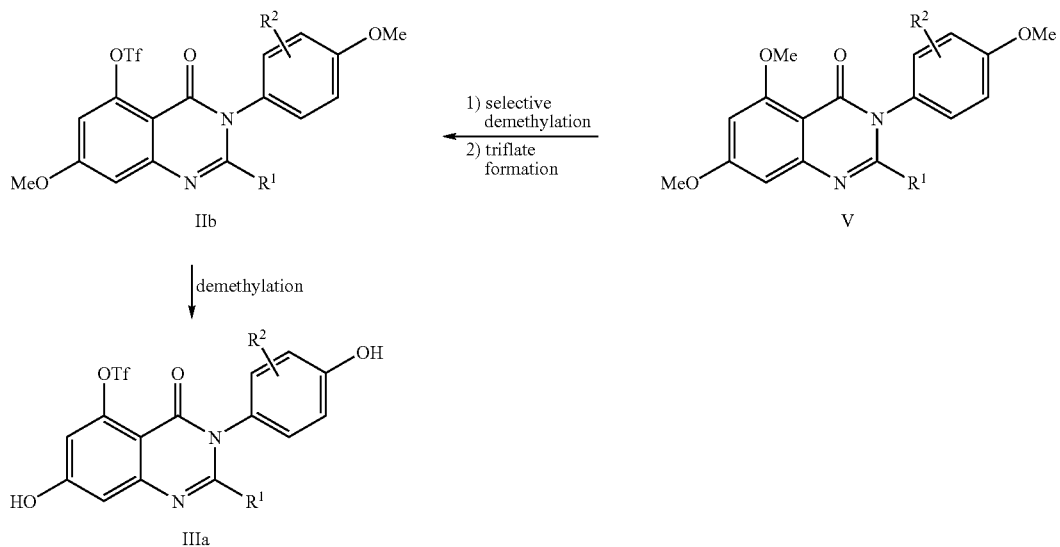

SCHEME 4

Compounds of the formula V may be prepared by reaction of the appropriately substituted orthoester with amides of the formula VI, or by acylation with the appropriate acid chloride followed by cyclization/dehydration (e.g. under heating in a high boiling solvent, with or without molecular sieves). Alternatively, benzoxazinones of the formula VII may be reacted directly with anilines VIII to provide compounds of the formula V. Compounds of the formula VIII may be reacted with the isatoic anhydride IX to provide compounds of the formula VI. Compounds VII and IX may be prepared from the known intermediates X by treatment with either the appropriate orthoester, or with phosgene, respectively. Anilines of the formula VIII are either commercially available, known in the literature, or can be prepared according to the synthesis of similar analogs prepared in the literature.

Utilities and Combinations

A. Utilities

The compounds of the present invention modulate the function of the estrogen receptor beta (ERβ), and include compounds which are, for example, selective agonists, partial agonists, antagonists or partial antagonists of the ERβ. Thus, the present compounds are useful in the treatment of a condition or disorder which can be treated by modulating the function or activity of an ERβ in a subject, wherein treatment comprises prevention, partial alleviation or cure of the condition or disorder. Modulation may occur locally, for

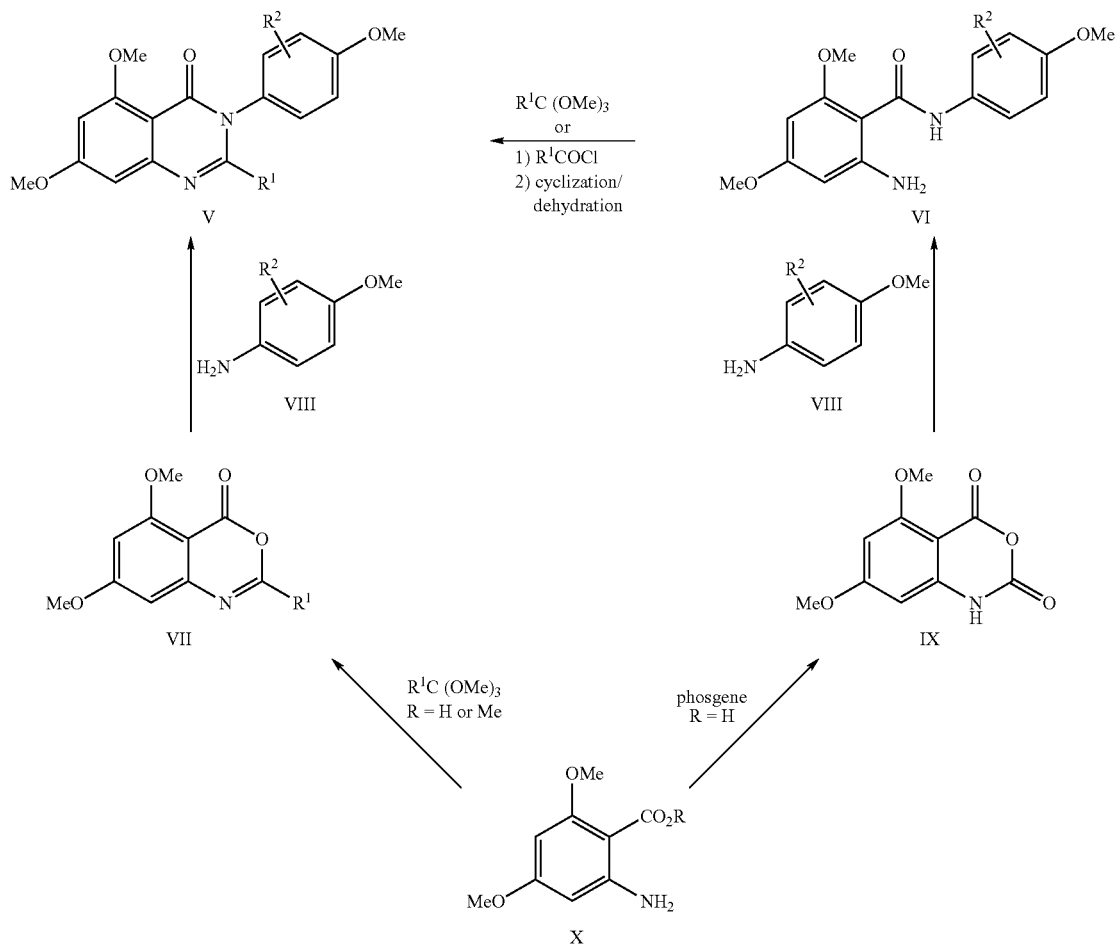

SCHEME 5

One may obtain addition salts, particularly pharmaceutically acceptable addition salts, from the compounds of formula I. For example, the compounds of formula I may contain an acidic free phenol or thiol group, such as the salts of sodium, potassium and calcium. Alternatively, the compounds of formula I may contain an amino group, such as an inorganic or organic acid, for example, hydrochloride, methanesulfonate, acetate, maleate, succinate, fumarate, sulfate, lactate or citrate.

example, within certain tissues of the subject, or more extensively throughout a subject being treated for such a condition or disorder.

Accordingly, the compounds of the present invention can be administered to mammals, preferably humans, for the treatment of a variety of conditions and disorders, including, but not limited to bone disorders, e.g., osteoporosis (including glucocorticoid-induced osteoporosis), osteopenia, Paget's disease and peridontal disease; cardiovascular diseases (including fibroproliferative conditions); hypercholesterolemia; hypertriglyceridemia; vasomotor disorders (e.g., hot flashes); urogenital disorders (e.g., urinary incontinence); prostatic hypertrophy; endometrial hyperplasia; and cancer, including prostate cancer, uterine cancer, ovarian cancer, breast cancer and endometrial cancer. Further, the compounds of the present invention may have central nervous system action and therefore may be useful for the treatment of multiple CNS disorders, such as neurodegenerative diseases (e.g., improvement of cognitive function and the treatment of dementia, including Alzheimer's disease and short-term memory loss).

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s) or other pharmaceutically active materials.

For example, the compounds of the present invention may be employed in combination with other modulators of the estrogen receptor beta and/or with other suitable therapeutic agents useful in the treatment of the aforementioned disorders, such as, but not limited to, anti-osteoporosis agents, cholesterol lowering agents, growth promoting agents, modulators of bone resorption and cardiovascular agents.

Examples of suitable anti-osteoporosis agents for use in combination with the compounds of the present invention include bisphosphonates (e.g., alendronate, risedronate, ibandronate and zolendrate), parathyroid hormone, PTH fragments and PTH analogues (e.g. PTH-(1-84) and PTH-(1-34)) and calcitonins.

Examples of suitable cholesterol lowering agents for use in combination with the compounds of the present invention include HMG-CoA reductase inhibitors (e.g., pravastatin, lovastatin, atorvastatin, simvastatin, NK-104 (a.k.a. itavastatin, nisvastatin or nisbastatin) and ZD-4522 (a.k.a. rosuvastatin, atavastatin or visastatin)), MTP inhibitors, fibrates (e.g., gemfibrozil) and bile acid sequestrants.

Examples of suitable growth promoting agents for use in combination with the compounds of the present invention include growth hormone secretagogues, such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or with growth hormone releasing factor and its analogs or growth hormone and its analogs or somatomedins including IGF-1 and IGF-2, or with alpha-adrenergic agonists, such as clonidine or serotinin 5-HT$_D$ agonists, such as sumatriptan, or agents which inhibit somatostatin or its release, such as physostigmine and pyridostigmine.

Examples of suitable modulators of bone resorption for use in combination with the compounds of the present invention include estrogen; selective estrogen receptor modulators (e.g., tamoxifen, lasofoxifene, TSE-424 and raloxifene); selective androgen receptor modulators, such as those disclosed in Edwards, *Bio. Med. Chem. Let.*, 1999 9, 1003-1008 and *J. Med. Chem.*, 1999 42, 210-212; hormone replacement therapies; vitamin D and analogues thereof (e.g., 1,25-dihydroxy vitamin D3); elemental calcium and calcium supplements; cathepsin K inhibitors; chloride channel inhibitors (e.g., ClC-7 inhibitors); MMP inhibitors; vitronectin receptor antagonists; Src SH$_2$ antagonists; Src kinase inhibitors; vacular H$^+$-ATPase inhibitors; osteoprotegrin; Tibolone; p38 inhibitors; prostanoids; PPAR gamma antagonists or isoflavinoids (e.g., genistein and ipriflavone); androgens (e.g., testosterone and dihydrotestosterone); RANK ligand antagonists; TRAP inhibitors; AP-1 inhibitors and progesterone receptor agonists (e.g., medroxyprogesterone acetate (MPA)).

Examples of suitable cardiovascular agents for use in combination with the compounds of the present invention include vasopeptidase inhibitors, ACE inhibitors, x-reductase inhibitors, muscarinic Ach antagonists, acetylcholinesterase inhibitors, angiotensin II receptor antagonists, thrombin inhibitors, Factor Xa inhibitors, tissue plasminogen activators, streptokinase, or other thrombolytic or antithrombotic agents. Compounds of formula I and their physiologically acceptable salts, prodrug esters or stereoisomers thereof may be formulated for administration via any suitable means, for example, orally, such as in the form of tablets, capsules, granules or powders; rectally, such as in the form of suppositories; nasally, including administration to the nasal membranes, such as by inhalation spray; topically (including buccal and sublingual); vaginal or parental (including intramuscular, sub-cutaneous, intravenous, and directly into the affected tissue) administration or in a form suitable for administration by inhalation or insufflation. The formulations may, where appropriate, be conveniently presented in discrete dosage units and may be prepared by any of the methods well known in the art of pharmacy. All methods may include the step of bringing into association the active compound with liquid carriers or finely divided solid carriers, or both, and then if necessary, shaping the product into the desired formulation.

The active principle may be in the form of a solid or a liquid and can be utilized in a composition such as tablet, capsule, ointment, solution or suspension, or in other suitable carrier materials. Examples of suitable carrier materials are iontophoetic devices, rectal suppositories, transdermal systems, granules, injectable preparations, or the like, prepared according to procedures known in the art. Further, the active principle comprising a pharmaceutically effective amount of at least one compound of formula I, either alone or in combination, or in combination with one or more other active agent(s) may be incorporated with excipients normally employed in therapeutic medicines, such as talc, gum arabic, lactose, starch, magnesium stearate, polyuidone, cellulose derivatives, cacao butter, semisynthetic glycerides, aqueous or non-aqueous vehicles, fats of animal or vegetable origin, glycols, various wetting agents, dispersants or emulsifiers, silicone gels, stabilizers, certain polymers or copolymers, preservatives, binders, flavorings, colors and the like, as called for by acceptable pharmaceutical practice.

Dosage of the active principle required for use in treatment may vary not only with the particular compound selected, but also with the route of administration, the nature of the condition being treated and the age and condition of the patient. In general, however, a suitable dose will be in the range of from about 0.0002 to 300 mg/kg of body weight per day, particularly from about 0.02 to 50 mg/kg of body weight per day, on a regimen of single or 2 to 4 divided daily doses. For example, for an adult with an average weight of 60 to 70 Kg, the dosage of active principle can vary between 1 and 500 mg when administered orally, in one or more daily doses, or from 0.01 to 50 mg, when administered parenterally in one or more daily dosages.

The above other therapeutic agents, when employed in combination with the compounds of the present invention, may be used, for example, in those amounts indicated in the Physicians' Desk Reference (PDR) or as otherwise determined by one of ordinary skill in the art.

EXAMPLES

The following examples serve to better illustrate, but not limit, some of the preferred embodiments of the invention.

ABBREVIATIONS

The following abbreviations are employed in the Examples:
AcOEt=ethyl acetate
AcOH=acetic acid
aq.=aqueous
Ar=argon
BINAP=2,2'-bis(diphenylphosphino)-1,1'-binaphthyl
Bn=benzyl
BOC=tert-butoxycarbonyl
BOP reagent=benzotriazol-1-yloxy-tris (dimethylamino) phosphonium hexafluorophosphate
br=broad
Bu=butyl
c=concentration
° C.=degrees Centigrade
CAN=ceric ammonium nitrate
CBZ=carbobenzyloxy or carbobenzoxy or benzyloxycarbonyl
$CDCl_3$=chloroform-d
$CD_3OD$=methanol-$d_4$
$CH_2Cl_2$=dichloromethane
$CHCl_3$=chloroform
$CH_3CN$=acetonitrile
$CO_2$=carbon dioxide
$Cs_2CO_3$=cesium carbonate
d=day(s) or doublet
DBU=1,8-diazabicyclo[5.4.0]undec-7-ene
DDQ=2,3-dichloro-5,6-dicyano-1,4-benzoquinone
DEAD=diethylazodicarboxylate
DIAD=diisopropylazodicarboxylate
DIBAL=diisobutylaluminum hydride
DMA=N,N-dimethylacetamide
DMAP=4-dimethylaminopyridine
DME=1,2-dimethoxyethane
DMF=dimethylformamide
DMSO=dimethylsulfoxide
EDC=3-ethyl-3'-(dimethylamino)propylcarbodiimide hydrochloride
ES+=electrospray positive ionization
ES−=electrospray positive ionization
Et=ethyl
$Et_3N$=triethylamine
EtOAc=ethyl acetate
$Et_2O$=diethyl ether
EtOH=ethanol
FMOC=fluorenylmethoxycarbonyl
g=gram(s)
h=hour(s)
HCl=hydrochloric acid
hex=hexane or hexanes
$HNO_3$=nitric acid
$H_2O$=water
HOAc=acetic acid
HOAT=1-hydroxy-7-azabenzotriazole
HOBT=1-hydroxybenzotriazole hydrate
HPLC=high performance liquid chromatography
$H_3PO_4$=phosphoric acid
$H_2SO_4$=sulfuric acid
Hz=hertz
iPr=isopropyl
$iPr_2NEt$=diisopropylethylamine
iPrOH=isopropanol
$K_2CO_3$=potassium carbonate
KF=potassium fluoride
KHMDS=potassium bis(trimethylsilyl)amide
$KHSO_4$=potassium hydrogen sulfate
KOH=potassium hydroxide
KOTMS=potassium trimethylsilanolate
L=liter(s)
LAH=lithium aluminum hydride
LC/MS=high performance liquid chromatography/mass spectrometry
$LiAlH_4$=lithium aluminum hydride
LiHMDS=lithium bis(trimethylsilyl)amide
LiOH=lithium hydroxide
m=multiplet
M=molar
mCPBA=3-chloroperoxybenzoic acid
Me=methyl
MeOH=methanol
meq=milliequivalent(s)
mg=milligram(s)
$MgCl_2$=magnesium chloride
$MgSO_4$=magnesium sulfate
MHz=megahertz
μL=microliter(s)
min=minute(s)
mL=milliliter(s)
mm=millimeter(s)
mmol=millimole(s)
$MnO_2$=manganese dioxide
mol=mole(s)
mp=melting point
MS or Mass Spec=mass spectrometry
m/z=mass to charge ratio
$N_2$=nitrogen
$NaBH_4$=sodium borohydride
$NaBH(OAc)_3$=sodium triacetoxyborohydride
$NaCNBH_3$=sodium cyanoborohydride
$NaHCO_3$=sodium bicarbonate
NaHMDS=sodium bis(trimethylsilyl)amide
NaOH=sodium hydroxide
NaOEt=sodium ethoxide
NaOMe=sodium methoxide
NaSMe=sodium thiomethoxide
$Na_2SO_4$=sodium sulfate
nBuLi=n-butyllithium
$NEt_3$=triethylamine
$NH_4Cl$=ammonium chloride
$NH_4OH$=ammonium hydroxide
NMM=N-methylmorpholine
NMO=N-methylmorpholine N-oxide
NMP=N-methylpyrrolidinone
NMR=nuclear magnetic resonance
Pd/C=palladium on carbon
$Pd(dppf)Cl_2$—$CH_2Cl_2$=[1,1'-bis(diphenylphosphino)ferrocene]dichloropalladium(II) complex with dichloromethane (1:1)
$Pd(OAc)_2$=palladium acetate
Ph=phenyl
$Ph_3P$=triphenylphosphine
$(Ph_3P)_4Pd$=tetrakistriphenylphosphine palladium
$P_2O_5$=phosphorus pentoxide
$POCl_3$=phosphorus oxychloride Pr=propyl
PtO$_2$=platinum oxide
PXPd$_2$=bis[di-tert-butylphosphinous chloride-□P]di-µ-chlorodipalladium
RT=room temperature
s=singlet
sat or sat'd=saturated
SOCl$_2$=thionyl chloride
t=triplet
TBS=tert-butyldimethylsilyl
tBu=tertiary butyl
TFA=trifluoroacetic acid
THF=tetrahydrofuran
Ti(OiPr)$_4$=titanium isopropoxide
TLC=thin layer chromatography
TMEDA=N,N,N',N'-tetramethylethylenediamine
TMS=trimethylsilyl or trimethylsilane
UV=ultraviolet HPLC analysis of the exemplified compounds was carried out under one of the following reverse phase methods, with the appropriate method and retention time noted in the Examples.

Method A: YMC S5 ODS 4.6×50 mm column, gradient elution 0-100% B/A over 4 min (solvent A=10% MeOH/H$_2$O containing 0.2% H$_3$PO$_4$, solvent B=90% MeOH/H$_2$O containing 0.2% H$_3$PO$_4$), flow rate 4 mL/min, UV detection at 220 nm.

Method B: Zorbax SB C18 4.6×75 mm column, gradient elution 0-100% B/A over 8 min (solvent A=10% MeOH/H$_2$O containing 0.2% H$_3$PO$_4$, solvent B=90% MeOH/H$_2$O containing 0.2% H$_3$PO$_4$), flow rate 2.5 mL/min, UV detection at 220 nm.

Preparative reverse phase HPLC purification of the exemplified compounds was carried out under one of the following methods, with the appropriate method and conditions noted in the Examples.

Method 1: YMC S5 ODS 30×100 mm column; solvent A=10% MeOH/H$_2$O containing 0.1% TFA, solvent B=90% MeOH/H$_2$O containing 0.1% TFA; flow rate 40 mL/min; TV detection at 220 nm.

Method 2: YMC S5 ODS 30×250 mm column; solvent A=10% MeOH/H$_2$O containing 0.1% TFA, solvent B=90% MeOH/H$_2$O containing 0.1% TFA; flow rate 25 mL/min; UV detection at 220 nm.

Example 1

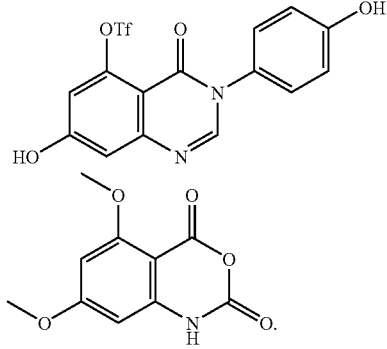

A

To a cooled (0° C.) brown solution of 4,6-dimethoxy anthranilic acid (76.0 g, 0.385 mol), [Newman, H.; Angier, R. B. *J. Org. Chem.*, 1969, 34(11), 3484] in THF (1.3 L) was added triphosgene (40.0 g, 0.135 mol) in portions over a 20 min period. After 30 min, the reaction was warmed to room temperature and stirred for an additional 1.5 h. The reaction mixture was poured into cold (0° C.) water (4 L). Additional water (2 L) was added to facilitate the stirring of the thick solid formed. After stirring for 30 min, the reaction mixture was filtered to give a beige solid. The solid was washed with water, air-dried, and then dried under high vacuum to give 79.2 g (92%) of the 4,6-dimethoxyisatoic anhydride.

MS (ES−) m/z 221.9 (M−H)$^-$
HPLC: Retention time=3.58 min (Method B)
$^1$H NMR (400 MHz, DMSO-d$_6$): δ 11.51 (bs, 1H), 6.36 (d, J=1.76 Hz, 1H), 6.20 (d, J=1.76 Hz, 1H), 3.86 (s, 3H), 3.85 (s, 3H).

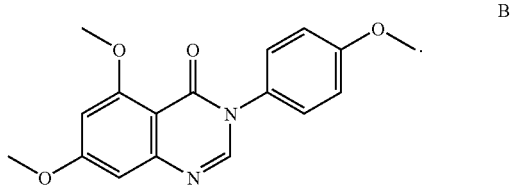

B

A mixture of the Part A compound (50 g, 0.224 mol), p-anisidine (68.9 g, 0.560 mol) and N,N-dimethylaminopyridine (2.73 g, 0.022 mol) in anhydrous DMA (500 mL) was warmed to 110° C. A clear brown solution formed at 80-90° C. and gas evolution was observed (CO$_2$ loss). After 24 h, the reaction was cooled to room temperature, diluted with water (1 L), and extracted with ethyl acetate (3×500 mL). The combined organic layers were washed with brine (250 mL), dried over MgSO$_4$, filtered, and concentrated to give a brown residue (85.2 g). The residue was dissolved in anhydrous triethylorthoformate (720 mL) and warmed to reflux for 4 hr. Upon cooling to room temperature, an off-white solid precipitated. Filtration, washing with triethylorthoformate (1 L), air drying, and drying under high vacuum gave 55.1 g (79%) of the quinazolinone as an off-white solid.

MS (ES+) m/z 313.1 (M+H)$^+$
HPLC: Retention time=6.35 min (Method B)
$^1$H NMR (400 MHz, DMSO-d$_6$): δ 8.17 (s, 1H), 7.37 (d, 2H, J=8.8 Hz), 7.06 (d, 2H, J=8.8 Hz), 6.73 (d, 1H, J=2.2 Hz), 6.62 (d, 1H, J=2.2 Hz), 3.9 (s, 3H), 3.83 (s, 3H), 3.82 (s, 3H).

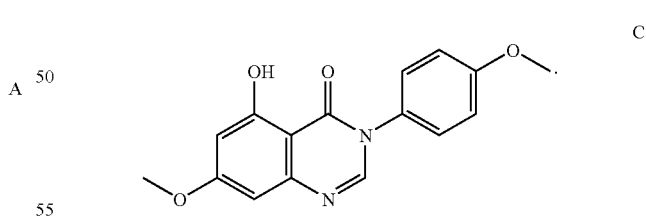

C

A suspension of the Part B compound (2.40 g, 7.68 mmol) and anhydrous lithium chloride (6.51 g, 153.6 mmol) in anhydrous DMF (51.2 mL) was warmed to 135° C. After 3 to 5 min. the starting material completely dissolved, then after approximately 10 min a voluminous precipitate formed. The precipitate redissolved after 20 min and the resulting solution was stirred at 135° C. for 2.5 h. After cooling to room temperature, the reaction was poured into water (100 mL) and acidified with 1.0 N HCl to give a white precipitate. The resulting mixture was extracted with CH$_2$Cl$_2$ (3×). The combined organic layers were washed with brine, dried over MgSO₄, filtered, and concentrated in vacuo to give a white suspension in DMF. Filtration provided 1.10 g (48%) of the Part C compound as a white solid.

MS (ES+) m/z 299.1 (M+H)⁺

HPLC: Retention time=3.18 min (Method A)

¹H NMR (400 MHz, DMSO-d₆) δ ppm: 11.77 (s, 1H), 8.26 (s, 1H), 7.48 (d, J=8.4 Hz, 2H), 7.10 (d, J=8.8 Hz, 2H), 6.72 (d, J=2.2 Hz, 1H), 6.54 (d, J=1.3 Hz, 1H), 3.88 (s, 3H), 3.83 (s, 3H).

Alternative Procedure for Selective Deprotection of the Part B Compound with Boron Tribromide:

To a cooled (0° C.) clear, yellow solution of the Part B (106 mg, 0.339 mmol) in CH₂Cl₂ (3.40 mL) was added dropwise boron tribromide (0.032 mL, 0.339 mmol). The reaction stirred at 0° C. for 1 h and then warmed to room temperature. After 5.5 h, the reaction was diluted with ethyl acetate (10 mL). The reaction was cooled to 0° C. and saturated NaHCO₃ (5 mL) was added dropwise. The mixture was stirred for 20 min, then the layers were separated. The aqueous layer was extracted with methylene chloride (2×5 mL) and ethyl acetate (2×5 mL). The combined organic layers were washed with brine, dried over MgSO₄, filtered, and concentrated to give 90 mg (89%) of the Part C compound as an off-white solid weighing.

To a cooled (0° C.) clear, yellow solution of the Part D compound (1.88 g, 4.36 mmol) in methylene chloride (43.6 mL) was added dropwise over 5 min boron tribromide (6.20 mL, 65.5 mmol). The reaction was stirred at 0° C. for 1 h, and then warmed to room temperature. After 7 days, the reaction was added dropwise to a vigorously stirred, cold (ice bath) mixture of ethyl acetate (150 mL) and saturated NaHCO₃ (100 mL). The mixture was stirred for 10 min, then the layers were separated. The aqueous layer was extracted with ethyl acetate (2×20 mL). The combined organic layers were washed with brine, dried over MgSO₄, filtered, and concentrated to give an orange foam weighing 2.47 g. Column chromatography (5% methanol in methylene chloride) gave 1.63 g (93%) of the title compound as a white foam.

MS (ES+) m/z 402.9 (M+H)⁺

HPLC: Retention time=5.60 min (Method B)

¹H NMR (400 MHz, DMSO-d₆) δ: 11.39 (s, 1H), 9.86 (s, 1H), 8.29 (s, 1H), 7.28 (d, J=8.6 Hz, 2H), 7.08 (bs, 1H), 6.95 (bs, 1H), 6.90 (d, J=8.6 Hz, 2H).

Example 2

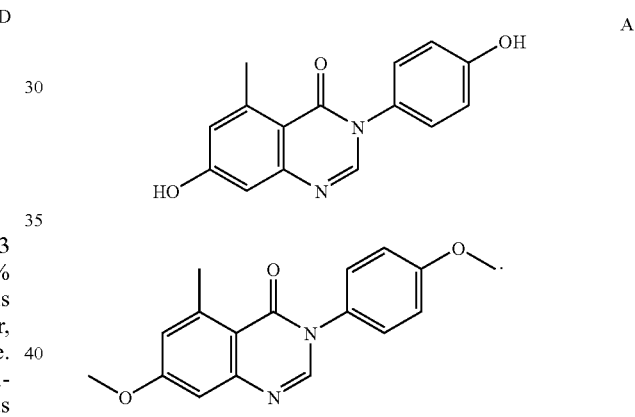

To a cooled (0° C.) solution of the Part C compound (5.83 g, 19.54 mmol) in DMF (65 mL) was added in portions 60% sodium hydride in mineral oil (1.01 g, 25.41 mmol). Gas evolution was observed and after 30 min at 0° C., the clear, slightly yellow solution was warmed to room temperature. After 30 min, the reaction was cooled to 0° C. and N-phenyl-trifluoromethanesulfonimide (7.33 g, 20.52 mmol) was added. The reaction was stirred at 0° C. for 30 min and then warmed to room temperature. After 30 min, the reaction was quenched with saturated ammonium chloride and diluted with water (150 mL). The reaction was extracted with ethyl acetate (3×60 mL). The combined organic layers were washed with brine, dried over MgSO₄, filtered and concentrated to give an off-white solid. Column chromatography (1:1 hexane:ethyl acetate) provided 7.13 g (85%) of the Part D compound as a white solid.

MS (ES+) m/z 430.9 (M+H)⁺

HPLC: Retention time=6.77 min (Method B)

¹H NMR (400 MHz, CDCl₃) δ: 8.09 (s, 1H), 7.32 (d, J=8.8 Hz, 2H), 7.18 (d, J=2.2 Hz, 1H), 7.03 (d, J=8.8 Hz, 2H), 6.92 (d, J=2.2 Hz, 1H), 3.96 (s, 3H), 3.85 (s, 3H).

A flame-dried flask containing the Example 1 Part D compound (0.300 g, 0.697 mmol), Pd(dppf)Cl₂—CH₂Cl₂ (0.114 g, 0.139 mmol), potassium phosphate tribasic (0.592 g, 2.78 mmol), and methylboronic acid (0.166 g, 2.78 mmol) was purged with argon for 10 min, then degassed THF (4.65 mL) was added. The resulting dark red-purple mixture was placed in a preheated oil bath (73° C.). After 5 h, the reaction was cooled to room temperature, diluted with methylene chloride (20 mL), washed with water (5 mL) and brine (5 mL), and filtered through a plug of Celite®. The filtrate was dried over MgSO₄, filtered and concentrated to give an off-white solid weighing 0.282 g. Column chromatography (1:1 hexane: ethyl acetate) gave 0.174 g (84%) of the Part A compound as a white solid.

HPLC: Retention time=6.29 min (Method B)

¹H NMR (500 MHz, CDCl₃) δ: 8.03 (s, 1H); 7.31 (d, J=8.8 Hz, 2H); 7.03 (d, J=8.8 Hz, 2H); 7.00 (d, J=2.5 Hz, 1H); 6.86 (d, J=2.5 Hz, 1H); 3.92 (s, 3H), 3.86 (s, 3H), 2.82 (s, 3H).

¹³C NMR (125 MHz, CDCl₃) δ: 163.35, 161.22, 159.82, 151.93, 146.73, 143.61, 130.39, 128.42, 119.31, 114.76, 114.54, 106.92, 55.62, 55.52, 23.44.

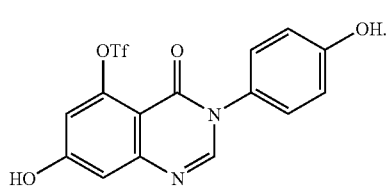

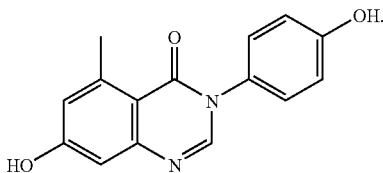

To a clear, colorless solution of the Part A compound (0.035 g, 0.118 mmol) in methylene chloride (0.60 mL) was added dropwise boron tribromide (0.22 mL, 2.36 mmol). The resulting clear, yellow solution stirred at room temperature. After 19 h, the reaction was diluted with methylene chloride (5 mL). The reaction was then added dropwise to a vigorously stirred cold (ice bath) mixture of ethyl acetate/saturated NaHCO$_3$. The mixture was stirred for 10 min, then the layers were separated. The organic layer was washed with brine, dried over MgSO$_4$, filtered, and concentrated to give a white solid weighing 0.070 g. Column chromatography (7.5% methanol in methylene chloride) gave 0.0277 g (87%) of the title compound as a white solid.

MS (ES+) m/z 269.0 (M+H)$^+$

HPLC: Retention time=4.30 min (Method B)

$^1$H NMR (500 MHz, DMSO-d$_6$) δ: 10.44 (s, 1H), 9.79 (s, 1H), 8.10 (s, 1H), 7.23 (d, J=8.8 Hz, 2H), 6.87 (d, J=8.8 Hz, 2H), 6.81 (d, J=2.2 Hz, 1H), 6.76 (d, J=2.2 Hz, 1H), 2.67 (s, 3H).

Example 3

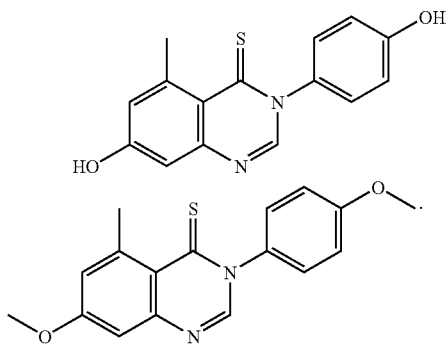

A yellow suspension of the Example 2 Part A compound (0.124 g, 0.42 mmol) and Lawesson's reagent (1.18 g, 2.93 mmol) in m-xylene (2.0 mL) was warmed to 145° C. After 44 h, additional Lawesson's reagent (0.590 g, 1.46 mmol) was added and the reaction was stirred at 145° C. for an additional 26 h. The reaction was cooled to room temperature, diluted with methylene chloride, filtered, and concentrated to give an orange solid weighing 0.865 g. Column chromatography (1.5:1 hexane:ethyl acetate) gave 0.0599 g (46%) of the Part A compound as a yellow solid.

HPLC: Retention time=7.33 min (Method B)

$^1$H NMR (400 MHz, CDCl$_3$) δ: 8.13 (s, 1H); 7.23 (d, J=8.8 Hz, 2H); 7.04 (d, J=8.8 Hz, 2H), 7.02 (d, J=2.2 Hz, 1H), 6.97 (d, J=2.2 Hz, 1H), 3.93 (s, 3H), 3.88 (s, 3H), 3.07 (s, 3H).

$^{13}$C NMR (125 MHz, CDCl$_3$) δ: 187.39, 162.89, 159.80, 147.82, 145.38, 145.31, 135.24, 128.95, 124.61, 122.24, 114.96, 107.27, 55.59, 55.51, 27.99.

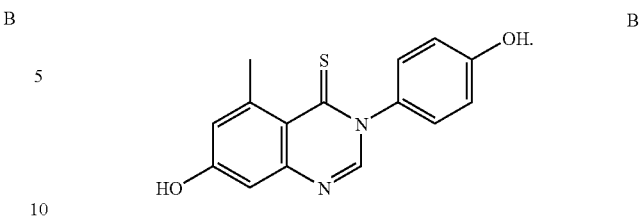

To a cooled (0° C.) clear, yellow solution of the Part A compound (0.0599 g, 0.191 mmol) in methylene chloride (1.91 mL) was added dropwise boron tribromide (0.09 mL, 0.958 mmol). The resulting clear, dark orange solution was stirred at 0° C. for 30 min, and then warmed to room temperature. After 9 h, the reaction was then added dropwise to a vigorously stirred cold (ice bath) mixture of ethyl acetate/saturated NaHCO$_3$. The mixture was stirred for 10 min, then the layers were separated. The aqueous layer was extracted with ethyl acetate (2×). The combined organic layers were washed with brine, dried over MgSO$_4$, filtered, and concentrated to give a orange solid weighing 0.063 g. The crude material was adsorbed onto silica gel (0.200 g). Column chromatography (5% methanol in methylene chloride) gave 0.0252 g (46%) of the title compound as a yellow solid.

MS (ES+) m/z 284.9 (M+H)$^+$

HPLC: Retention time=5.49 min (Method B)

$^1$H NMR (500 MHz, MeOD$_4$) δ: 8.20 (s, 1H); 7.11 (d, J=8.8 Hz, 2H); 6.91-6.87 (m, 4H), 2.99 (s, 3H).

$^{13}$C NMR (125 MHz, MeOD$_4$) δ: 188.73, 163.19, 159.17, 148.56, 147.36, 146.79, 135.72, 130.28, 124.80, 123.23, 117.07, 110.50, 28.28.

HRMS m/z Calc'd for C$_{15}$H$_{13}$N$_2$O$_2$S (M+H)$^+$: 285.0698. Found 285.0696.

Example 4

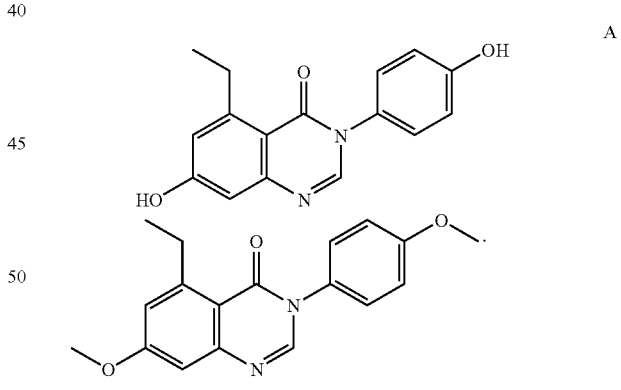

A flame-dried flask containing the Example 1 Part D compound (0.300 g, 0.697 mmol), Pd(dppf)Cl$_2$—CH$_2$Cl$_2$ (0.114 g, 0.139 mmol), and potassium phosphate tribasic (0.592 g, 2.78 mmol) was purged with argon for 10 min, then degassed THF (6.97 mL) and 1.0 M triethylborane (2.78 mL, 2.78 mmol) were added. The resulting rust-colored mixture was placed in a preheated oil bath (75° C.). After 5.5 h, the black reaction was cooled to room temperature, diluted with methylene chloride (15 mL), washed with water and brine, dried over MgSO$_4$, filtered and concentrated to give a black solid. Column chromatography (1:1 hexane:ethyl acetate) gave 0.168 g (78%) of the Part A compound as an off-white solid.

HPLC: Retention time=6.77 min (Method B)

¹H NMR (400 MHz, CDCl₃) δ: 8.05 (s, 1H), 7.32 (d, J=9.0 Hz, 2H), 7.04 (d, J=9.0 Hz, 2H), 7.01 (d, J=2.4 Hz, 1H), 6.90 (d, J=2.4 Hz, 1H), 3.93 (s, 3H), 3.86 (s, 3H), 3.27 (q, J=7.5 Hz, 2H), 1.26 (t, J=7.5 Hz, 3H).

¹³C NMR (125 MHz, CDCl₃) δ: 163.54, 160.55, 159.76, 152.20, 149.78, 146.59, 130.45, 128.40, 118.00, 114.75, 113.82, 106.90, 55.60, 55.51, 28.90, 15.72.

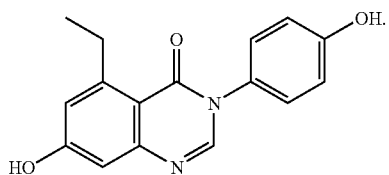
B

To a cooled (0° C.) clear, slightly yellow solution of the Part A compound (0.085 g, 0.274 mmol) in methylene chloride (2.74 mL) was added dropwise boron tribromide (0.39 mL, 4.10 mmol). Within minutes a white precipitate formed which redissolved over time. The reaction was stirred at 0° C. for 1 h, then warmed to room temperature. After 17 h the reaction was diluted with methylene chloride (5 mL). The reaction was then added dropwise to a vigorously stirred cold (ice bath) mixture of ethyl acetate/saturated NaHCO₃. The mixture was stirred for 10 min, then the layers were separated. The aqueous layer was extracted with ethyl acetate (2×). The combined organic layers were washed with brine, dried over MgSO₄, filtered, and concentrated to give an off-white solid. The crude material was adsorbed onto silica gel (0.600 g). Column chromatography (5% methanol in methylene chloride) gave 0.0443 g (57%) of the title compound as a white solid.

MS (ES+) m/z 283.0 (M+H)⁺

HPLC: Retention time=4.85 min (Method B)

¹H NMR (400 MHz, DMSO-d₆) δ: 8.11 (s, 1H), 7.24 (d, J=8.8 Hz, 2H), 6.87 (d, J=8.8 Hz, 2H), 6.83 (d, J=2.4 Hz, 1H), 6.78 (d, J=2.4 Hz, 1H), 3.13 (q. J=7.3 Hz, 2H), 1.14 (q, J=7.3 Hz, 3H).

Example 5

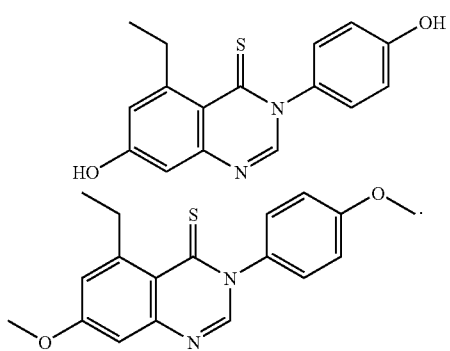

A yellow suspension of the Example 4 Part A compound (0.116 g, 0.373 mmol) and Lawesson's reagent (0.755 g, 1.87 mmol) in m-xylene (2.0 mL) was warmed to 145° C. After 72 h, additional Lawesson's reagent (1.51 g, 3.74 mmol) was added and the reaction was stirred at 145° C. for an additional 24 h. The reaction was cooled to room temperature, diluted with methylene chloride (40 mL), filtered, and concentrated to give a dark brown solid weighing 0.773 g. Column chromatography (2:1 hexane:ethyl acetate) gave 0.0211 g (17%) of the Part A compound as a yellow solid.

MS (ES+) m/z 327.1 (M+H)⁺

HPLC: Retention time=7.62 min (Method B)

¹H NMR (500 MHz, CDCl₃) δ: 8.17 (s, 1H), 7.23 (d, J=8.8 Hz, 2H), 7.04-6.95 (m, 4H), 3.94 (s, 3H), 3.88 (s, 3H), 3.65 (q, J=7.4 Hz, 2H), 1.29 (t, J=7.4 Hz, 3H).

¹³C NMR (125 MHz, CDCl₃) δ: 186.58, 163.18, 159.76, 151.08, 145.13, 135.30, 128.95, 124.08, 120.84, 114.93, 107.03, 55.60, 55.50, 30.35, 16.02.

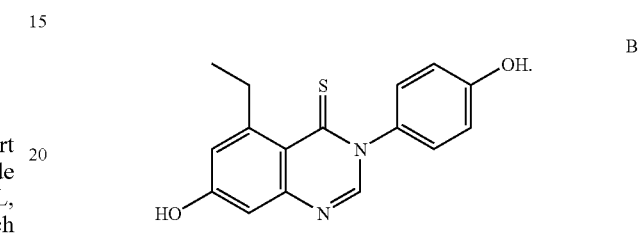
B

To a cooled (0° C.) clear, yellow solution of the Part A compound (0.0211 g, 0.0646 mmol) in methylene chloride (0.65 mL) was added dropwise boron tribromide (0.09 mL, 0.97 mmol). The resulting orange solution was stirred at 0° C. for 30 min and then warmed to room temperature. After 8 h, the reaction was then added dropwise to a vigorously stirred cold (ice bath) mixture of ethyl acetate/saturated NaHCO₃. The mixture was stirred for 10 min, then the layers were separated. The aqueous layer was extracted with ethyl acetate (2×). The combined organic layers were washed with brine, dried over MgSO₄, filtered, and concentrated to give an orange solid weighing 0.0192 g. Column chromatography (5% methanol in methylene chloride) gave 0.0117 g (60%) of the title compound as a yellow foam.

MS (ES+) m/z 298.9 (M+H)⁺

HPLC: Retention time=5.89 min (Method B)

¹H NMR (500 MHz, MeOD₄) δ: 8.22 (s, 1H); 7.12 (d, J=8.2 Hz, 2H); 6.92-6.88 (m, 4H), 3.61 (q, J=7.2 Hz, 2H), 1.25 (t, J=7.2 Hz, 3H).

¹³C NMR (125 MHz, MeOD₄) δ: 187.94, 163.46, 159.14, 152.69, 148.87, 147.07, 135.83, 130.29, 124.20, 122.04, 117.05, 110.51, 31.25, 16.79.

Example 6

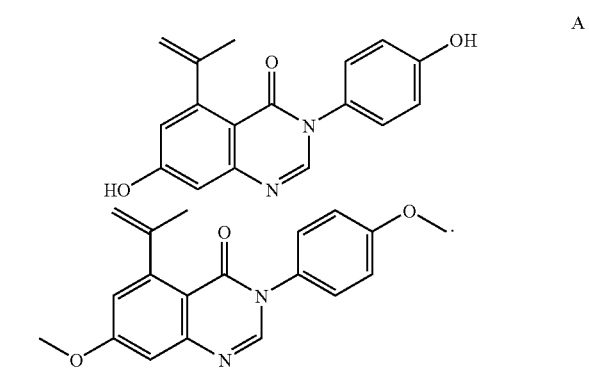

Isopropenyl magnesium bromide (0.5 M in tetrahydrofuran, 0.93 mL, 0.464 mmol) was added dropwise to a 0.5 M solution of zinc chloride in tetrahydrofuran (0.93 mL, 0.464 mmol). A mild exotherm was observed and a white precipitate formed. The resulting suspension was stirred at room temperature for 1.5 h. In a separate flamed-dried flask was placed the Example 1 Part D compound (0.100 g, 0.232 mmol) and tetrakis(triphenylphosphine) palladium (0.0404 g, 0.035 mmol). The vessel was purged with argon for 10 min and then degassed THF (1.16 mL) was added. To the clear, yellow solution was added the isopropenyl zinc halide suspension prepared above. The resulting bright yellow suspension was placed in a preheated oil bath (75° C.) for 2 h. The reaction was cooled to room temperature, quenched with saturated ammonium chloride and extracted with ethyl acetate (3×). The combined organic layers were washed with brine, dried over MgSO$_4$, filtered and concentrated to give a yellow foam weighing 0.120 g. Column chromatography (1:1 hexane:ethyl acetate) provided 0.052 g (69%) of the Part A compound as a pale yellow foam.

HPLC: Retention time=6.75 min (Method B)

$^1$H NMR (400 MHz, CDCl$_3$) δ: 8.08 (s, 1H); 7.32 (d, J=9.0 Hz, 2H); 7.08 (d, J=2.6 Hz, 1H), 7.01 (d, J=9.0 Hz, 2H), 6.86 (d, J=2.6 Hz, 1H), 5.09 (d, J=1.3 Hz, 1H), 4.85 (d, J=1.3 Hz, 1H), 3.94 (s, 3H), 3.85 (s, 3H), 2.10 (s, 3H).

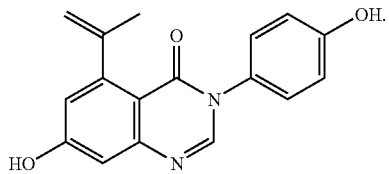

B

To a cooled (0° C.) clear, slightly yellow solution of the Part A compound (0.052 g, 0.161 mmol) in methylene chloride (1.61 mL) was added dropwise boron tribromide (0.10 mL, 1.16 mmol). The reaction was stirred at 0° C. for 1 h, and then warmed to room temperature. After 15 h the reaction was cooled to 0° C. and additional boron tribromide (0.10 mL, 1.16 mmol) was added. The reaction was warmed to room temperature. After 24 h, additional boron tribromide (0.10 mL, 1.16 mmol) was again added. The resulting milky-white mixture was stirred for 72 h. The reaction was diluted with methylene chloride (2 mL). The reaction was then added dropwise to a vigorously stirred cold (ice bath) mixture of ethyl acetate/saturated NaHCO$_3$. The mixture was stirred for 10 min, then the layers were separated. The aqueous layer was extracted with ethyl acetate (2×). The combined organic layers were washed with brine, dried over MgSO$_4$, filtered, and concentrated to give a yellow-brown solid weighing 0.043 g. Column chromatography (5% methanol in methylene chloride) gave 0.0395 g (83%) of the title compound as a white solid.

MS (ES+) m/z 295.0 (M+H)$^+$

HPLC: Retention time=4.95 min (Method B)

$^1$H NMR (400 MHz, CDCl$_3$) δ: 8.16 (s, 1H); 7.23 (d, J=8.8 Hz, 2H); 6.96 (d, J=2.8 Hz, 1H), 6.92 (d, J=8.8 Hz, 2H), 6.75 (d, J=2.8 Hz, 1H), 5.01 (d, J=1.4 Hz, 1H), 4.77 (d, J=1.4 Hz, 1H), 2.05 (s, 3H).

Example 7

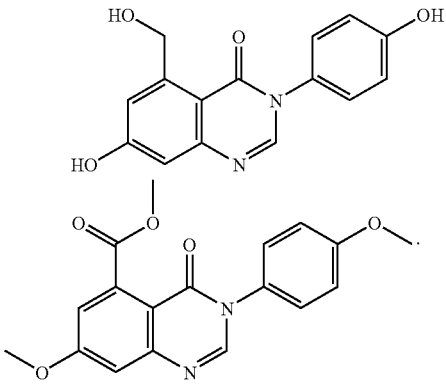

A

To a flame-dried flask was placed the Example 1 Part D compound (0.250 g, 0.581 mmol), palladium acetate (0.0130 g, 0.058 mmol), and diphenylphosphinopropane (0.0240 g, 0.058 mmol). Next, dimethylsulfoxide (1.81 mL), methanol (1.16 mL), and triethylamine (0.17 mL) were added. Carbon monoxide (balloon) was bubbled through the cloudy, yellow mixture for 5 min and the vessel was maintained under a carbon monoxide atmosphere. The reaction was placed in a preheated oil bath (70° C.) and a clear, slightly yellow solution formed. After 15 h, additional palladium acetate (0.0130 g, 0.058 mmol), diphenylphosphinopropane (0.0240 g, 0.058 mmol), methanol (1.16 mL), and triethylamine (0.17 mL) were added. The reaction was purged with carbon monoxide (balloon) as described above. The reaction was placed in a preheated oil bath (70° C.). After 2 h, the dark orange reaction was cooled to room temperature. The reaction was diluted with water (6 mL) and extracted with methylene chloride (3×5 mL). The combined organic layers were washed with brine, dried over MgSO$_4$, filtered and concentrated to give an orange solid. Column chromatography (1:1 hexane:ethyl acetate) provided 0.166 g (84%) of the ester as a white solid.

HPLC: Retention time=5.56 min (Method B)

$^1$H NMR (400 MHz, CDCl$_3$) δ: 8.08 (s, 1H), 7.32 (d, J=9.0 Hz, 2H), 7.19 (d, J=2.2 Hz, 1H), 7.05 (d, J=2.2 Hz, 1H), 7.02 (d, J=9.0 Hz, 2H), 3.96 (s, 3H), 3.95 (s, 3H), 3.85 (s, 3H).

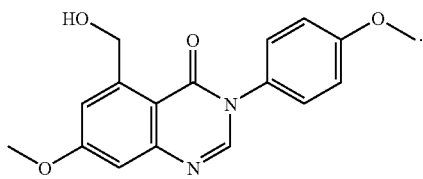

B

To a cooled (0° C.) suspension the Part A compound (0.083 g, 0.243 mmol) in THF (1.21 mL) was added dropwise 1.0M lithium aluminum hydride in THF (0.24 mL). The resulting clear, yellow-brown solution stirred at 0° C. Over the course of the reaction a precipitate formed. After 4 h, the reaction was quenched with saturated ammonium chloride and diluted with ethyl acetate. The layers were separated and the aqueous layer was extracted with ethyl acetate (2×). The combined organic layers were washed with brine and dried over MgSO$_4$, filtered and concentrated to give a yellow residue weighing 0.063 g. The crude material was dissolved in ethanol (1.0 mL) to give a clear, yellow solution. Next 2,3-dichloro-5,6-dicyano-1,4-benzoquinone (0.048 g, 0.213 mmol) was added. The resulting clear, orange solution was stirred at room temperature. A precipitate formed and additional ethanol (2 mL) was added to facilitate stirring. After 4 h, the excess solvent was removed and the reaction was purified directly. Column chromatography (5% methanol in methylene chloride) gave 0.070 g (92%) of the Part B compound as an off-white solid.

MS (ES+) m/z 312.9 (M+H)+

HPLC: Retention time=5.18 min (Method B)

$^1$H NMR (400 MHz, CDCl$_3$) δ: 8.10 (s, 1H), 7.33 (d, J=9.2 Hz, 2H), 7.12 (d, J=2.6 Hz, 1H), 7.10-7.04 (m, 3H), 4.88 (d, J=7.9 Hz, 2H), 4.72 (t, J=7.9 Hz, 1H), 3.95 (s, 3H), 3.88 (s, 3H).

$^{13}$C NMR (125 MHz, CDCl$_3$) δ: 164.10, 161.84, 160.12, 152.77, 146.55, 144.75, 129.90, 128.33, 118.94, 114.95, 113.92, 108.52, 65.37, 55.77, 55.65.

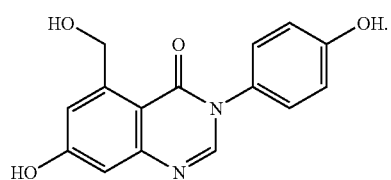

C

To a cooled (0° C.) suspension of the Part B compound (0.040 g, 0.128 mmol) in methylene chloride (1.28 mL) was added dropwise boron tribromide (0.24 mL, 2.56 mmol). The suspension was stirred at 0° C. for 30 min, and then warmed to room temperature to give a clear, orange solution. After 24 h, the reaction was then added dropwise to a vigorously stirred cold (ice bath) mixture of ethyl acetate/saturated NaHCO$_3$. The mixture was stirred for 10 min, then the layers were separated. The aqueous layer was extracted with ethyl acetate (2×). The combined organic layers were washed with brine, dried over MgSO$_4$, filtered, and concentrated to give the benzyl bromide as an off-white solid weighing 0.0525 g.

To a clear, slightly brown solution of the crude benzyl bromide in acetonitrile (1.5 mL) was added potassium acetate (0.0444 g, 0.453 mmol) and 18-crown-6 (0.120 g, 0.453 mmol). The reaction was warmed to 50° C. After 15 h, the clear, colorless reaction was cooled to room temperature and 1.0M sodium hydroxide (0.60 mL, 0.604 mmol) was added. The biphasic mixture was stirred vigorously for 5 h. The reaction was acidified to pH 4 with 1.0M hydrogen chloride. The reaction was extracted with ethyl acetate (2×). The combined organic layers were washed with brine, dried over MgSO$_4$, filtered and concentrated to a slightly purple solid weighing 0.153 g. Column chromatography (5% methanol in methylene chloride) gave 0.017 g as an off-white solid which was 93% pure. Purification by preparative HPLC (Method 1; 30-90% B; 10 min gradient) gave 0.0123 g (34%) of the title compound as white solid.

MS (ES+) m/z 284.9 (M+H)+

HPLC: Retention time=3.44 min (Method B)

$^1$H NMR (400 MHz, DMSO-d$_6$) δ: 10.50 (s, 1H), 9.80 (s, 1H), 8.11 (s, 1H), 7.29 (d, J=2.5 Hz, 1H), 7.23 (dd, J=8.8, 2.2 Hz, 2H), 6.87 (d, J=8.8, 2.2 Hz, 2H), 6.83 (d, J=2.5 Hz, 1H), 5.26 (t, J=5.6 Hz, 1H), 4.98 (d, J=5.6 Hz, 2H).

Example 8

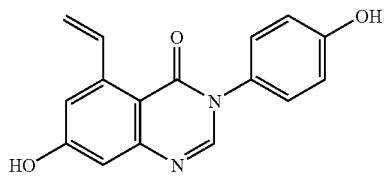

A flame-dried flask containing the Example 1 Part E compound (0.200 g, 0.497 mmol), bis(triphenylphosphine) palladium dichloride (0.035 g, 0.049 mmol), triphenylphosphine (0.052 g, 0.199 mmol), lithium chloride (0.084 g, 1.99 mmol) and 2,6-di-tert-butyl-4-methylphenol (a crystal) was purged with argon for 10 min. Next, dimethylformamide (degassed, 4.97 mmol) and tributylvinylstannane (0.29 mL, 0.99 mmol) were added. The reaction was placed in a preheated oil bath (120° C.). After 4 h, the cloudy yellow reaction was cooled to room temperature, diluted with water (15 mL), and extracted with ethyl acetate (3×) and methylene chloride (3×). The combined organic layers were washed with brine, dried over MgSO$_4$, filtered, and concentrated to give a viscous oil weighing 0.447 g. Column chromatography (5% methanol in methylene chloride) gave 0.069 g (50%) of the title compound as an off-white solid.

MS (ES−) m/z 278.8 (M−H)−

HPLC: Retention time=4.80 min (Method B)

$^1$H NMR (500 MHz, DMSO-d$_6$) δ: 10.60 (s, 1H), 9.81 (s, 1H), 8.14 (s, 1H), 7.91 (dd, J=17.4, 11.0 Hz, 1H), 7.24 (d, J=8.5 Hz, 2H), 7.05 (d, J=2.5 Hz, 1H), 6.93 (d, J=2.5 Hz, 1H), 6.87 (d, J=8.5 Hz, 2H), 5.58 (dd, J=17.4, 1.6 Hz, 1H), 5.28 (d, J=11.0 Hz, 1H).

Example 9

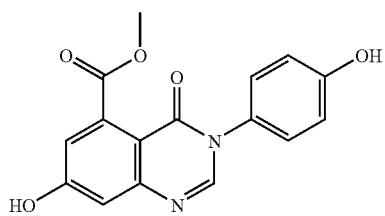

To a flame-dried flask was placed the Example 1 Part D compound (0.300 g, 0.746 mmol), palladium acetate (0.0168 g, 0.075 mmol), and diphenylphosphinopropane (0.0309 g, 0.075 mmol). Next, dimethylsulfoxide (2.3 mL), methanol (3.0 mL), and triethylamine (0.44 mL) were added. Carbon monoxide (balloon) was bubbled through the clear, yellow solution for 10 min and the vessel was maintained under a carbon monoxide atmosphere. The reaction was placed in a preheated oil bath (73° C.). After 5 h, the dark brown reaction was cooled to room temperature. The reaction was diluted with water (10 mL), acidified (pH=3) with 1.0M hydrochloric acid, and extracted with ethyl acetate (3×15 mL). The combined organic layers were washed with brine, dried over MgSO$_4$, filtered and concentrated to give an orange residue weighing 0.400 g. Column chromatography (5% methanol in methylene chloride) provided 0.0580 g (25%) of the title compound as a white solid.

MS (ES+) m/z 312.8 (M+H)+
HPLC: Retention time=4.12 min (Method B)
$^1$H NMR (400 MHz, DMSO-d$_6$) δ: 10.98 (s, 1H), 9.85 (s, 1H), 8.23 (s, 1H), 7.26 (d, J=8.8 Hz, 2H), 7.04 (d, J=2.2 Hz, 1H), 6.92 (d, J=2.2 Hz, 1H), 6.88 (d, J=8.8 Hz, 2H), 3.76 (s, 3H).

Example 10

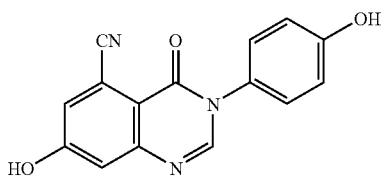

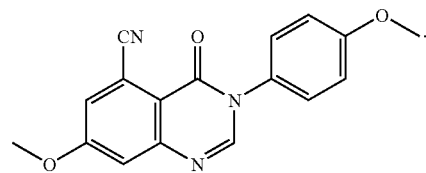

A

A flame-dried test-tube containing the Example 1 Part D compound (0.250 g, 0.581 mmol), tris(dibenzylideneacetone) dipalladium (0.0531 g, 0.058 mmol), and 1,1'-bis(diphenylphosphino)ferrocene (0.128 g, 0.232 mmol) was purged with argon for ten minutes. Next, degassed dimethylformamide (1.9 mL) was added and the reaction was placed in a preheated oil bath (90° C.) to give a clear, orange-brown solution. A suspension of zinc cyanide (0.0818 g, 0.697 mmol) in dimethylformamide (1.4 mL) was added in portions (0.2 mL every 15 min). Following the addition, the reaction was continued for 3 h. The reaction was cooled to room temperature, diluted with water (6 mL) giving an orangish-precipitate, which was extracted with methylene chloride (4×10 mL). The combined organic layers were washed with brine, dried over MgSO$_4$, filtered and concentrated to give an orange solid. Column chromatography (2:1 ethyl acetate:hexane) provided 0.148 g (83%) of the Part A compound as a faint orange solid.
MS (ES+) m/z 308.1 (M+H)+
HPLC: Retention time=5.40 min (Method B)
$^1$H NMR (400 MHz, CDCl$_3$) δ: 8.14 (s, 1H), 7.48 (d, J=2.6 Hz, 1H), 7.35-7.33 (m, 3H), 7.04 (d, J=8.8 Hz, 2H), 3.98 (s, 3H), 3.87 (s, 3H).

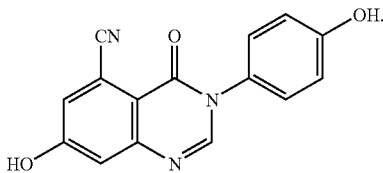

B

A suspension of the Part A compound (0.120 g, 0.393 mmol) and sodium ethanethiolate (0.662 g, 7.87 mmol) in dimethylformamide (4.0 mL) was warmed to 120° C. to give a clear, yellow solution. After 6.5 h, the reaction was cooled to 0° C. and diluted with water (12 mL). The reaction was acidified to pH 5 with the dropwise addition of 1N hydrochloric acid. The reaction was extracted with methylene chloride (3×10 mL). The combined organic layers were washed with brine (1×5 mL), dried over MgSO$_4$, filtered and concentrated to give a yellow solid weighing 0.264 g. The crude material was adsorbed onto silica gel (1.0 g). Column chromatography (7.5% methanol in methylene chloride) gave 0.027 g as yellow solid, which was further purified by preparative HPLC (Method 2; 0-100% B; 30 min. gradient). The fractions were combined and neutralized with saturated NaHCO$_3$ and the volume was reduced by approximately 80%. A few drops of 1N hydrochloric acid were added and concentrated to give a residue. Extraction with methanol and concentration gave 0.0047 g (4%) of the title compound as a faint yellow solid.
MS (ES-) m/z 277.8 (M-H)-
HPLC: Retention time=4.09 min (Method B)
$^1$H NMR (400 MHz, DMSO-d$_6$) δ: 8.24 (s, 1H), 7.34 (bs, 1H), 7.29 (d, J=8.8 Hz, 2H), 7.10 (bs, 1H), 6.88 (d, J=8.8 Hz, 2H).

Example 11

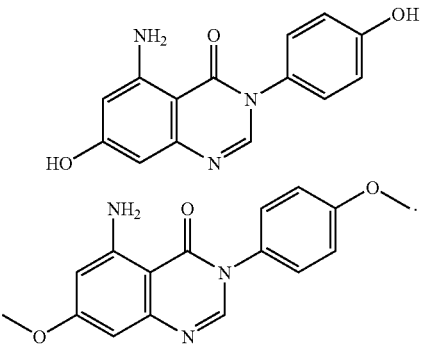

A

A flame-dried vessel containing the Example 1 Part D compound (0.933 g, 2.17 mmol), palladium acetate (0.0487 g, 0.217 mmol), (S)-BINAP (0.203 g, 0.326 mmol) and cesium carbonate (0.990 g, 3.04 mmol) was purged with argon for 10 min. Next, degassed THF (10.8 mL) was added followed by benzophenone imine (0.44 mL, 2.60 mmol). The resulting dark, orange solution was placed in a preheated oil bath (75° C.). After 24 h, the cloudy dark orange mixture was cooled to room temperature, diluted with diethyl ether (10 mL), and filtered through Celite®. Concentration gave a burgundy foam weighing 1.34 g. The burgundy foam was dissolved in THF (10.8 mL) and 1N hydrochloric acid (4.33 mL) was added. The reaction was stirred at room temperature for 3 h. The resulting clear orange solution was diluted with methylene chloride (50 mL) and quenched with saturated NaHCO$_3$. The layers were separated and the aqueous layer was extracted with methylene chloride (15 mL). The combined organic layers were washed with brine, dried over MgSO$_4$, filtered and concentrated to give a yellow solid weighing 1.34 g. Column chromatography (1:1 hexane:ethyl acetate) gave 0.471 g (73%) of the Part A compound as an off-white solid.
MS (ES+) m/z 298.1 (M+H)+
HPLC: Retention time=6.09 min (Method B)
$^1$H NMR (500 MHz, CDCl$_3$) δ: 7.92 (s, 1H), 7.30 (d, J=8.8 Hz, 2H), 7.03 (d, J=8.8 Hz, 2H), 6.49 (d, J=2.2 Hz, 1H), 6.22 (bs, 2H), 6.15 (d, J=2.2 Hz, 1H), 3.86 (s, 3H).

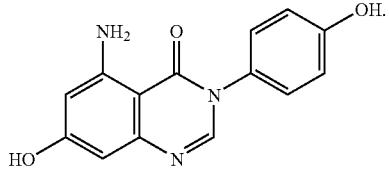

A clear, slightly yellow solution of the Part A compound (0.0245 g, 0.0.082 mmol) and sodium ethanethiolate (0.0693 g, 0.82 mmol) in dimethylformamide (0.82 mL) was warmed to 120° C. After 5 h, the reaction was cooled to 0° C. and diluted with water (2 mL). The reaction was acidified to pH 5 with the dropwise addition of 1N hydrochloric acid. The reaction was extracted with methylene chloride (3×) and ethyl acetate (3×). The combined organic layers were washed with brine, dried over MgSO$_4$, filtered and concentrated to give a brown solid weighing 0.026 g. The crude material was absorbed onto silica gel (0.250 g). Column chromatography (5% methanol in methylene chloride) gave 0.0086 g (39%) of the title compound as an off-white solid.

MS (ES+) m/z 270.1 (M+H)$^+$

HPLC: Retention time=3.92 min (Method B)

$^1$H NMR (400 MHz, DMSO-d$_6$) δ: 10.0 (bs, 1H), 9.80 (s, 1H), 7.94 (s, 1H), 7.21 (d, J=8.8 Hz, 2H), 7.17 (bs, 2H), 6.86 (d, J=8.8 Hz, 2H), 6.12 (d, J=2.2 Hz, 1H), 6.08 (d, J=2.2 Hz, 1H).

Example 12

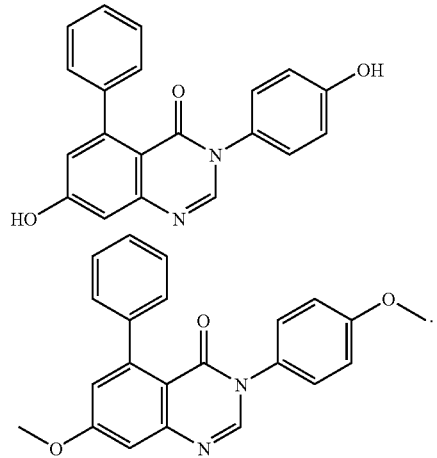

A flame-dried flask containing the Example 1 Part D compound (0.300 g, 0.697 mmol), Pd(dppf)Cl$_2$—CH$_2$Cl$_2$ (0.0853 g, 0.104 mmol), potassium phosphate tribasic (0.592 g, 2.78 mmol), and phenylboronic acid (0.340 g, 2.78 mmol) was purged with argon for 10 minutes. Next, degassed THF (7.0 mL) was added. The resulting dark orange suspension was placed in a preheated oil bath (73° C.). After 14 h, the dark red reaction was cooled to room temperature and diluted with ethyl acetate (20 mL). The reaction washed with water (5 mL), saturated NaHCO$_3$ (5 mL), and brine (5 mL), dried over MgSO$_4$, filtered and concentrated to give a burgundy residue weighing 0.667 g. Column chromatography (1:1 hexane:ethyl acetate) gave 0.216 g (86%) of the Part A compound as a white solid.

MS (ES+) m/z 359.15 (M+H)$^+$

HPLC: Retention time=6.97 min (Method B)

$^1$H NMR (400 MHz, CDCl$_3$) δ: 8.07 (s, 1H), 7.35-7.29 (m, 5H), 7.24 (d, J=8.9 Hz, 2H), 7.18 (d, J=2.6 Hz, 1H), 6.94 (d, J=8.9 Hz, 2H), 6.91 (d, J=2.6 Hz, 1H), 3.96 (s, 3H), 3.80 (s, 3H).

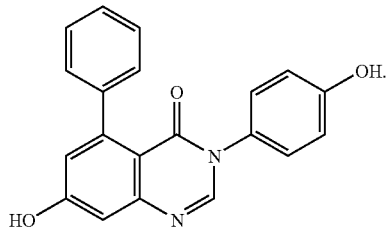

To a cooled (0° C.), clear, colorless solution of the Part A compound (0.095 g, 0.265 mmol) in methylene chloride (2.60 mL) was added dropwise boron tribromide (0.50 mL, 5.30 mmol). The resulting bright, yellow solution was stirred at 0° C. for 30 min and then warmed to room temperature. After 72 h, the reaction was added dropwise to a vigorously stirred cold (ice bath) mixture of ethyl acetate/saturated NaHCO$_3$. The layers were separated and the aqueous layer was extracted with ethyl acetate (2×). The combined organic layers were washed with brine, dried over MgSO$_4$, filtered, and concentrated to give an off-white solid. Trituration with ethyl acetate and filtration gave 0.0547 g (62%) of the title compound as a white solid.

MS (ES+) m/z 331.2 (M+H)$^+$

HPLC: Retention time=5.40 min (Method B)

$^1$H NMR (400 MHz, DMSO-d$_6$) δ: 10.69 (s, 1H), 9.76 (s, 1H), 8.22 (s, 1H), 7.33-7.22 (m, 5H), 7.18 (d, J=8.8 Hz, 2H), 6.99 (d, J=2.6 Hz, 1H), 6.82 (d, J=8.8 Hz, 2H), 6.70 (d, J=2.6 Hz, 1H).

While it is apparent that the embodiments of the invention herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present invention.

A number of references have been cited and the entire disclosures of which are incorporated herein by reference.

What is claimed is:

1. A compound according to Formula I, including all stereoisomers, prodrug esters and salts thereof:

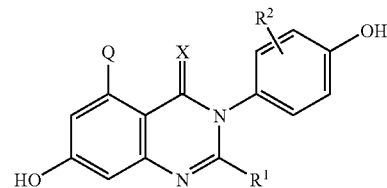

wherein,

Q is selected from the group consisting of alkyl, alkenyl, alkynyl, cycloalkyl, cycloalkenyl, aryl, amino, cyano, $CO_2R^3$, $CONR^4R^5$, $CH_2OH$ and $CH_2NH_2$;

X is selected from the group consisting of oxygen (O) and sulfur (S);

$R^1$ is selected from the group consisting of H and alkyl;

$R^2$ is selected from the group consisting of H, alkyl, alkoxy, halo, haloalkyl, haloalkoxy, trifluoromethyl, trifluoromethoxy and cyano;

$R^3$ is alkyl; and $R^4$ and $R^5$ are independently selected from the group consisting of H, alkyl, alkenyl alkynyl, cycloalkyl, aryl, and arylalkyl.

2. The compound according to claim 1, wherein:

Q is selected from the group consisting of alkyl, alkenyl, aryl, amino, cyano, $CO_2R^3$ and $CH_2OH$;

$R^1$ is H; and $R^2$ is selected from the group consisting of H, alkyl and halo.

3. The compound according to claim 2, wherein:

$R^2$ is H.

4. The compound according to claim 3, wherein:

Q is alkyl.

5. The compound according to claim 1, wherein the compound is selected from the group consisting of:

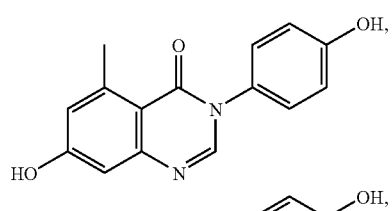

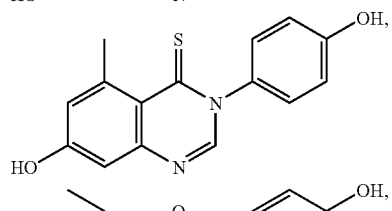

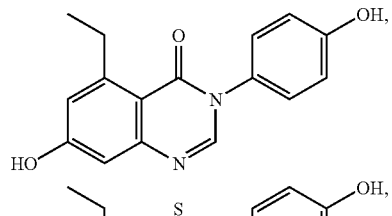

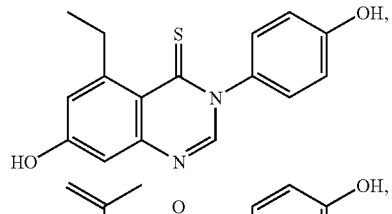

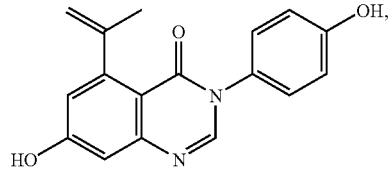

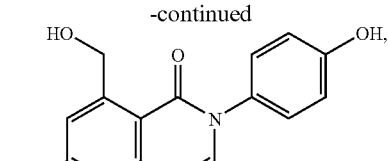

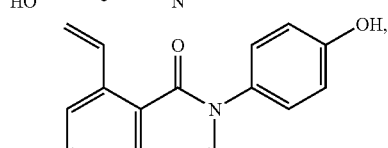

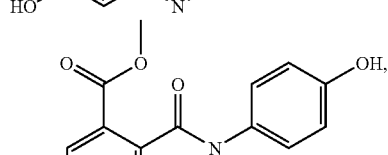

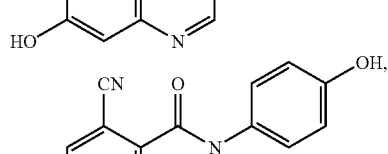

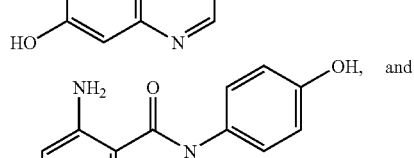

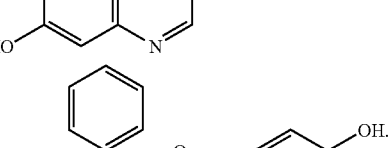

6. A pharmaceutical composition, comprising:

at least one compound according to claim 1; and at least one pharmaceutically acceptable carrier or diluent.

7. The pharmaceutical composition according to claim 6, further comprising:

at least one additional therapeutic agent.

8. A compound according to Formula I, including all stereoisomers, prodrug esters and salts thereof:

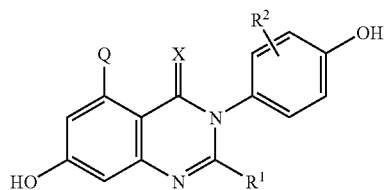

wherein,
Q is selected from the group consisting of alkyl, alkenyl, alkynyl, cycloalkyl, cycloalkenyl, aryl, $CO_2R^3$, $CONR^4R^5$, $CH_2OH$ and $CH_2NH_2$;
X is selected from the group consisting of oxygen (O) and sulfur (S);
$R^1$ is selected from the group consisting of H and alkyl;
$R^2$ is selected from the group consisting of H, alkyl, alkoxy, halo, haloalkyl, haloalkoxy, trifluoromethyl, trifluoromethoxy and cyano;
$R^3$ is alkyl; and
$R^4$ and $R^5$ are independently selected from the group consisting of H, alkyl, alkenyl alkynyl, cycloalkyl, aryl, and arylalkyl.

9. The compound according to claim 8, wherein:
Q is selected from the group consisting of alkyl, alkenyl, aryl, amino, cyano, $CO_2R^3$ and $CH_2OH$;
$R^1$ is H; and
$R^2$ is selected from the group consisting of H, alkyl and halo.

10. The compound according to claim 9, wherein:
$R^2$ is H and Q is alkyl.

11. The compound according to claim 8, wherein the compound is selected from the group consisting of:

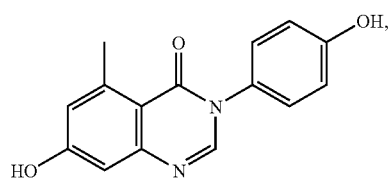

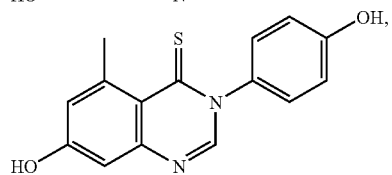

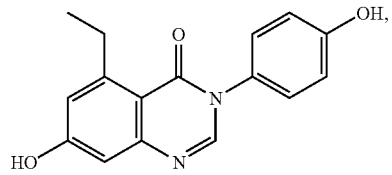

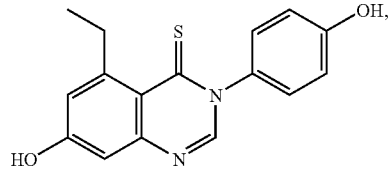

-continued

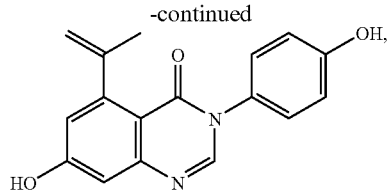

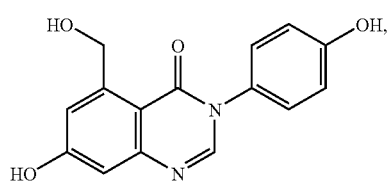

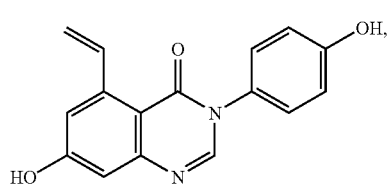

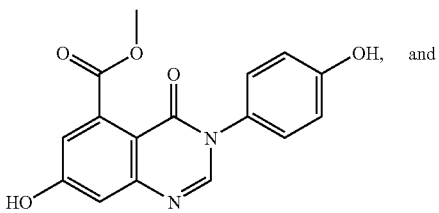

and

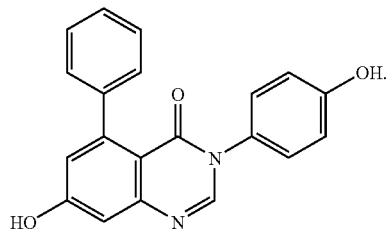

12. A pharmaceutical composition, comprising:
at least one compound according to claim 8; and
at least one pharmaceutically acceptable carrier or diluent.

13. The pharmaceutical composition according to claim 12, further comprising:
at least one additional therapeutic agent.

* * * * *

UNITED STATES PATENT AND TRADEMARK OFFICE
CERTIFICATE OF CORRECTION

PATENT NO. : 7,456,188 B1
APPLICATION NO. : 11/411456
DATED : November 25, 2008
INVENTOR(S) : James R. Corte et al.

It is certified that error appears in the above-identified patent and that said Letters Patent is hereby corrected as shown below:

At column 31, line 15, in Claim 1, after "alkenyl" insert -- , --.
At column 32, line 45, please delete the structure below as listed in the patent:

"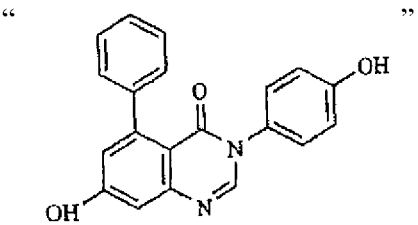"

and replace it with the correct structure listed below:

-- 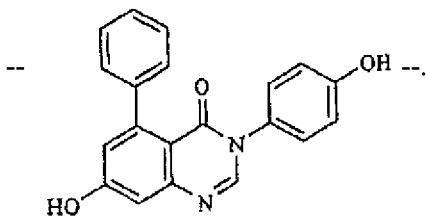 --.

At column 33, line 13, in Claim 8, after "alkenyl" insert -- , --.

Signed and Sealed this

Second Day of June, 2009

JOHN DOLL
*Acting Director of the United States Patent and Trademark Office*